United States Patent
Meskens

(10) Patent No.: US 11,577,087 B2
(45) Date of Patent: Feb. 14, 2023

(54) POWER AND DATA TRANSFER IN HEARING PROSTHESES

(71) Applicant: Cochlear Limited, Macquarie University (AU)

(72) Inventor: Werner Meskens, Opwijk (BE)

(73) Assignee: Cochlear Limited, Macquarie University (AU)

( * ) Notice: Subject to any disclaimer, the term of this patent is extended or adjusted under 35 U.S.C. 154(b) by 253 days.

(21) Appl. No.: 16/834,053

(22) Filed: Mar. 30, 2020

(65) Prior Publication Data

US 2020/0222701 A1 Jul. 16, 2020

Related U.S. Application Data

(63) Continuation of application No. 15/593,576, filed on May 12, 2017, now Pat. No. 10,632,317, which is a (Continued)

(51) Int. Cl.
*A61N 1/37* (2006.01)
*A61N 1/378* (2006.01)
(Continued)

(52) U.S. Cl.
CPC ....... *A61N 1/3787* (2013.01); *A61N 1/36036* (2017.08); *A61N 1/36038* (2017.08); (Continued)

(58) Field of Classification Search
CPC .............. A61N 1/3787; A61N 1/36036; A61N 1/36038; A61N 1/37223; A61N 1/37252;
(Continued)

(56) References Cited

U.S. PATENT DOCUMENTS 5,741,314 A 4/1998 Daly
8,103,353 B1 1/2012 Karunasiri
(Continued)

FOREIGN PATENT DOCUMENTS

KR 10-2006-0108251 A 10/2006

OTHER PUBLICATIONS

International Search Report and Written Opinion in counterpart International Application No. PCT/IB2015/050694, dated Jun. 11, 2015, 11 pages.

(Continued)

*Primary Examiner* — Unsu Jung
*Assistant Examiner* — Natasha Patel
(74) *Attorney, Agent, or Firm* — Edell, Shapiro & Finnan LLC

(57) ABSTRACT

Embodiments presented herein are generally directed to techniques for separately transferring power and data from an external device to an implantable component of a partially or fully implantable medical device. The separated power and data transfer techniques use a single external coil and a single implantable coil. The external coil is part of an external resonant circuit, while the implantable coil is part of an implantable resonant circuit. The external coil is configured to transcutaneously transfer power and data to the implantable coil using separate (different) power and data
(Continued)

time slots. At least one of the external or internal resonant circuit is substantially more damped during the data time slot than during the power time slot.

17 Claims, 7 Drawing Sheets

Related U.S. Application Data continuation of application No. 14/542,877, filed on Nov. 17, 2014, now Pat. No. 9,724,525.

(60) Provisional application No. 61/933,512, filed on Jan. 30, 2014.

(51) Int. Cl.
| | |
|---|---|
| *H02J 50/90* | (2016.01) |
| *H02J 50/80* | (2016.01) |
| *A61N 1/372* | (2006.01) |
| *A61N 1/36* | (2006.01) |
| *H02J 7/00* | (2006.01) |
| *H02J 50/12* | (2016.01) |
| *H04B 5/00* | (2006.01) |

(52) U.S. Cl.
CPC ..... *A61N 1/37223* (2013.01); *A61N 1/37252* (2013.01); *H02J 7/00034* (2020.01); *H02J 50/12* (2016.02); *H02J 50/80* (2016.02); *H02J 50/90* (2016.02); *H04B 5/0037* (2013.01); *H04R 2225/67* (2013.01)

(58) Field of Classification Search
CPC .. H02J 5/005; H02J 7/025; H02J 50/12; H02J 50/80; H02J 50/90; H02J 7/00034; H04B 5/0037; H04R 2225/67
See application file for complete search history.

(56) References Cited

U.S. PATENT DOCUMENTS

| | | | |
|---|---|---|---|
| 2002/0032471 A1* | 3/2002 | Loftin | A61N 1/37276 333/32 |
| 2004/0105411 A1 | 6/2004 | Boatwright | |
| 2007/0118185 A1 | 5/2007 | Shaquer | |
| 2007/0296393 A1* | 12/2007 | Malpas | A61B 5/0002 600/372 |
| 2008/0195177 A1 | 8/2008 | Ibrahim | |
| 2009/0216296 A1* | 8/2009 | Meskens | A61N 1/36036 607/57 |
| 2010/0204756 A1* | 8/2010 | Aghassian | A61N 1/37217 607/60 |
| 2011/0287717 A1 | 11/2011 | Ibrahim | |
| 2012/0109256 A1* | 5/2012 | Meskins | H04B 5/0093 607/57 |
| 2012/0306284 A1* | 12/2012 | Lee | H04B 5/0037 307/104 |
| 2013/0043735 A1* | 2/2013 | Low | H04B 5/0031 307/104 |
| 2013/0059537 A1 | 3/2013 | Ibrahim | |
| 2013/0108091 A1 | 5/2013 | Stoffaneller | |
| 2013/0123881 A1 | 5/2013 | Aghassian | |
| 2013/0214731 A1 | 8/2013 | Dinsmoor | |
| 2013/0289334 A1 | 10/2013 | Badstibner | |
| 2013/0310630 A1 | 11/2013 | Smith | |
| 2014/0021909 A1 | 1/2014 | Klawon | |
| 2014/0214123 A1 | 7/2014 | Janssen | |

OTHER PUBLICATIONS

Extended European Search Report issued in counterpart European Application No. 15743022.4, dated Aug. 11, 2017, 8 pages.
English Translation of Office Action in counterpart Korea Application No. 10-2016-7019559, dated Jan. 27, 2022, 12 pages.

\* cited by examiner

POWER AND DATA TRANSFER IN HEARING PROSTHESES

CROSS-REFERENCE TO RELATED APPLICATIONS

This application is a continuation application of U.S. Non-Provisional application Ser. No. 15/593,576 entitled "Power and Data Transfer in Hearing Prostheses," filed May 12, 2017, which is a continuation application of U.S. Non-Provisional application Ser. No. 14/542,877 entitled "Power and Data Transfer in Hearing Prostheses," filed Nov. 17, 2014, which in turn claims priority to U.S. Provisional Application No. 61/933,512 entitled "Power and Data Transfer in Hearing Prostheses," filed Jan. 30, 2014, the entire contents of which are hereby incorporated by reference.

BACKGROUND

Field of the Invention

The present invention relates generally to hearing prostheses, and more particularly, to power and data transfer in hearing prostheses.

Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing life saving and/or lifestyle enhancement functions for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional components perform diagnosis, prevention, monitoring, treatment or management of a disease or injury or symptom thereof, or to investigate, replace or modify of the anatomy or of a physiological process. Many of these functional components utilize power and/or data received from external components that are part of, or operate in conjunction with, the implantable medical device.

SUMMARY

In one aspect presented herein, an implantable medical device is provided. The implantable medical device comprises an implantable resonant circuit comprising an implantable coil, and an external resonant circuit comprising an external coil configured to transcutaneously transfer power and data to the implantable coil using separate power and data time slots. At least one of the external or implantable resonant circuit is substantially more damped during the data time slots than during the power time slots.

In another aspect presented herein, an external transmitter circuit is provided. The external transmitter circuit comprises an external resonant circuit comprising an external coil and one or more driver bridges configured to cause the external coil to transfer power and data to an implantable receiver circuit using separate power and data time slots. The quality factor of the external resonant circuit is lower during the data slots than during the power time slots.

In another aspect presented herein, an apparatus is provided. The apparatus comprises an implantable resonant circuit comprising an implantable coil, an external resonant-circuit comprising an external coil forming a transcutaneous power and data link with the implantable coil, and at least one driver bridge configured to drive the external coil so as to separately transfer power and data to the implantable coil. Operational characteristics of at least one of the implantable resonant circuit or the external resonant circuit are dynamically adjusted during transfer of data to the implantable coil.

In another aspect presented herein, a method for transmitting power from an external transmitter circuit to an implantable receiver circuit is provided. The external transmitter circuit comprises an external resonant circuit that includes an external coil, while the implantable receiver circuit comprise an implantable resonant circuit that includes an implantable coil. The method comprises driving the external resonant circuit with one or more driver bridges during a power time slot to cause the external coil to transfer power to the implantable receiver circuit. The method further comprises driving the external resonant circuit with one or more driver bridges during a data time slot to cause the external coil to transfer data to the implantable receiver circuit. The power and data time slots are different time slots and the external resonant circuit is driven such that the quality factor of the external resonant circuit is lower during the data slot than during the power time slot.

BRIEF DESCRIPTION OF THE DRAWINGS

Embodiments of the present invention are described herein in conjunction with the accompanying drawings, in which.

DETAILED DESCRIPTION

Embodiments presented herein are generally directed to techniques for separately transferring power and data from an external device to an implantable component of a partially or fully implantable medical device. The separated power and data transfer techniques use a single external coil and a single implantable coil. The external coil is part of an external resonant circuit, while the implantable coil is part of an implantable resonant circuit. The external coil is configured to transcutaneously transfer power and data to the implantable coil using separate (different) power and data time slots. At least one of the external or internal resonant circuit is substantially more damped during the data time slot than during the power time slot. In certain embodiments, the external and internal resonant circuits are resonant tank circuits.

Embodiments of the present invention are described herein primarily in connection with one type of implantable medical devices, namely partially implantable hearing prostheses comprising an external component and an internal (implantable component). Hearing prostheses include, but are not limited to, auditory brain stimulators, cochlear implants (also commonly referred to as cochlear implant devices, cochlear prostheses, and the like; simply "cochlear implants" herein), bone conduction devices, and mechanical stimulators. It is to be appreciated that embodiments of the present invention may be implemented in any partially or fully implantable medical device now known or later developed.

Figure 1:
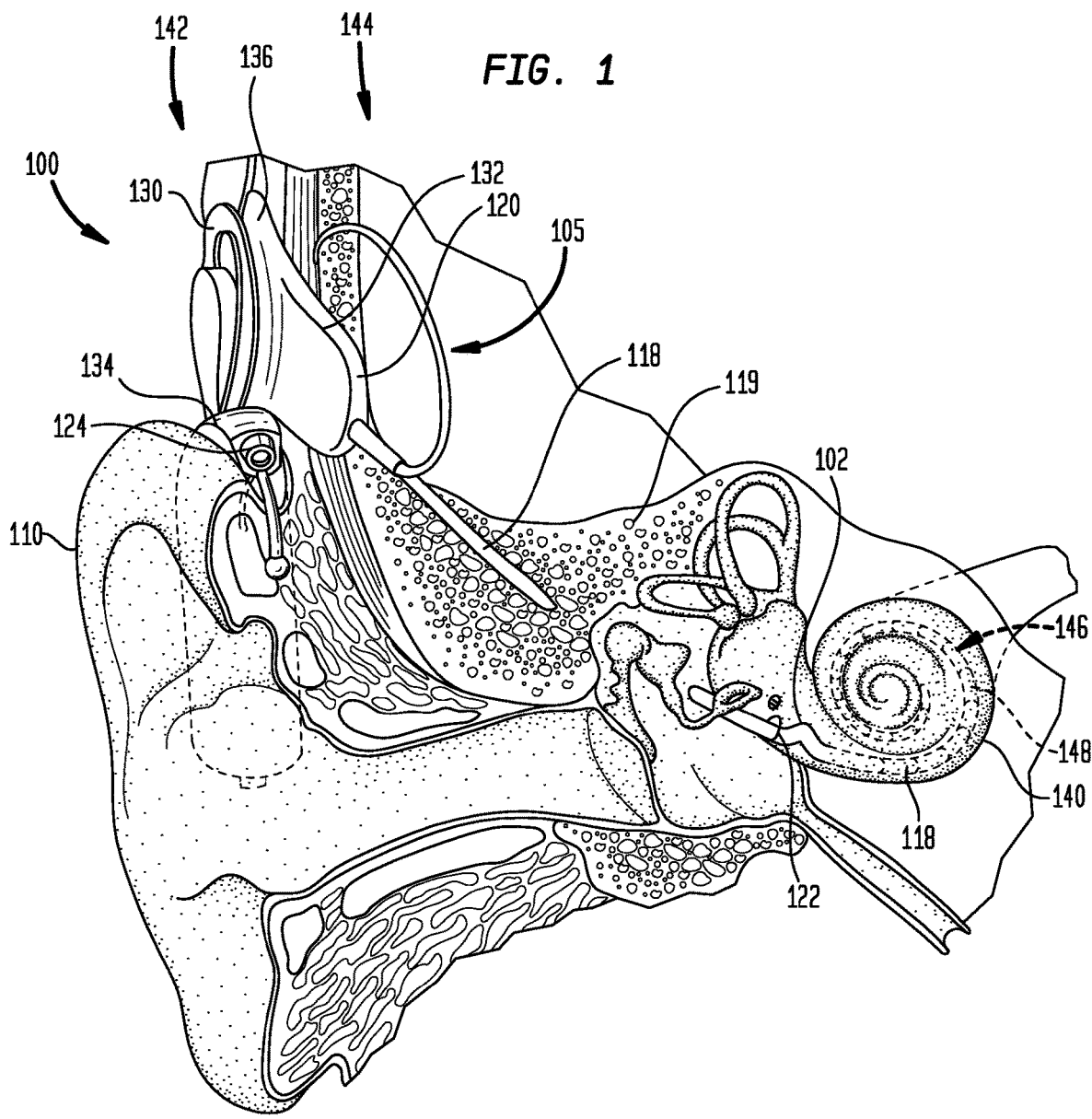
FIG. 1 illustrates an implantable hearing prostheses configured to implement separated power and data transfer techniques in accordance with embodiments presented herein.

FIG. 1 is a perspective view of an exemplary cochlear implant 100 configured to implement separated power and data transfer techniques in accordance with embodiments presented herein. The cochlear implant 100 includes an external component 142 and an internal or implantable component 144. The external component 142 is directly or indirectly attached to the body of the recipient and typically comprises one or more sound input elements 124 (e.g., microphones, telecoils, etc.) for detecting sound, a sound processor 134, a power source (not shown), an external coil 130 and, generally, a magnet (not shown) fixed relative to the external coil 130. The sound processor 134 processes electrical signals generated by a sound input element 124 that is positioned, in the depicted embodiment, by auricle 110 of the recipient. The sound processor 134 provides the processed signals to a transmitter circuit configured to drive (activate) external coil 130.

As used herein, an "external component" refers to one or more elements or devices that are part of, or operate in conjunction with, the implantable medical device. In other words, an external component may form part of the implantable medical device or may be a separate device that operates with an implantable medical device.

Returning to the example of FIG. 1, the implantable component 144 comprises an implant body 105, a lead region 108, and an elongate stimulating assembly 118. The implant body 105 comprises a stimulator unit 120, an implantable (internal) coil 136, and an internal receiver/transceiver unit 132, sometimes referred to herein as transceiver unit 132. The transceiver unit 132 is connected to the internal coil 136 and, generally, a magnet (not shown) fixed relative to the internal coil 136. Internal transceiver unit 132 and stimulator unit 120 are sometimes collectively referred to herein as a stimulator/transceiver unit 120.

Implantable coil 136 is typically a wire antenna coil comprised of multiple turns of electrically insulated single-strand or multi-strand platinum or gold wire. The electrical insulation of implantable coil 136 is provided by a flexible silicone molding. In use, transceiver unit 132 may be positioned in a recess of the temporal bone of the recipient.

The magnets in the external component 142 and implantable component 144 facilitate the operational alignment of the external coil 130 with the implantable coil 136. The operational alignment of the coils enables the external coil 130 to transmit/receive power and data to the implantable coil 136. As described further below, the external component 142 is configured to transmit electrical signals (i.e., power and data) from external coil 130 to implantable coil 136 using separate time slots over a radio frequency (RF) link.

Elongate stimulating assembly 118 is implanted in cochlea 140 and includes a contact array 146 comprising a plurality of stimulating contacts 148. Stimulating assembly 118 extends through cochleostomy 122 and has a proximal end connected to stimulator unit 120 via lead region 108 that extends through mastoid bone 119. Lead region 108 couples the stimulating assembly 118 to implant body 105 and, more particularly, stimulator/transceiver unit 120. The stimulating contacts 148 may be electrical contacts, optical contacts, or a combination of optical and electrical contacts.

As noted above, a transcutaneous RF link is provided to transfer power and data from external component 142 to implantable component 144. Certain conventional transcutaneous RF links use an amplitude modulated signal where the data and the power are transferred simultaneously (i.e., at the same time) over the same RF coil for extraction by the implantable component. In other words, the data signals are embedded in the power signals for simultaneous transmission from the external coil to the implantable coil. RF links that simultaneously transmit power and data are sometimes referred to as combined power and data links.

Other conventional arrangements use time multiplexing of pure power and data signals on separate RF links from different power and data transmitters. More specifically, in such arrangements a first RF link is created between a first external coil and an implantable coil. This first RF link is used solely for data transmission. Additionally, a second RF link is created between a second (different) external coil and the implantable coil. This second RF link is used solely for power transmission. A time multiplexing scheme is implemented such that either the first RF link or the second RF link is activated and at one time in order to avoid interference between the power and data signals. In other words, these arrangements use a first RF link (and first external coil) that is dedicated to data transmission and a second RF link (and second external coil) that is dedicated to power transmission where the first and second links are alternatively activated.

Presented herein are separated power and data transfer techniques in which a single transcutaneous RF link is used to separately transfer power and data from an external component to an implantable component. In accordance with the separated power and data transfer techniques, transfer of power and data occur during separate (different) time slots using the same external coil 130 (i.e., a shared external coil for both data and power). For example, a single transmission sequence/frame may be split into a power time slot (block) and a data time slot (block) and repeated. All of the power towards the implantable component 144 is transferred during the power time slot.

In order to enable use of a single shared external coil for power and data transmission during different time slots, the operational characteristics of one or both of an external transmitter (or transceiver) or an implantable receiver (or transceiver) are dynamically adjusted between the power and data slots. More specifically, the implantable receiver includes an implantable resonant circuit (e.g., an implantable resonant tank circuit) comprising an implantable coil, while the external transmitter includes an external resonant circuit (e.g., an external resonant tank circuit) comprising an external coil configured to transcutaneously transfer power and data to the implantable coil using the separate power and data time slots. At least one of the external or internal resonant circuit is substantially more damped during the data time slot than during the power time slot. That is, the quality factor (Q) of one or both of the external circuit or the internal resonant circuit is reduced during data transmission (relative to the quality factor of one or both of the external circuit or the internal resonant circuit during power transmission).

For ease of illustrations, embodiments will be primarily described herein with reference to the use of external and implantable resonsant tank circuits. It is to be appreciated that embodiments may include other types of external and/or implantable resonant circuits.

As noted, the techniques presented herein involve switching between power transfer for some fraction of the frame, and then data transfer for another part of the frame. By decoupling the data from the power, the RF link can be optimized for efficient power transfer during the power time slots and then independently optimized for data transfer. For example, a very high quality factor may be used to optimize the power transfer efficiency during the power time slots. However, when switching to the data transfer mode, the internal or external tank circuit is dampened (and optionally detuned) to improve data integrity.

Figure 2A:
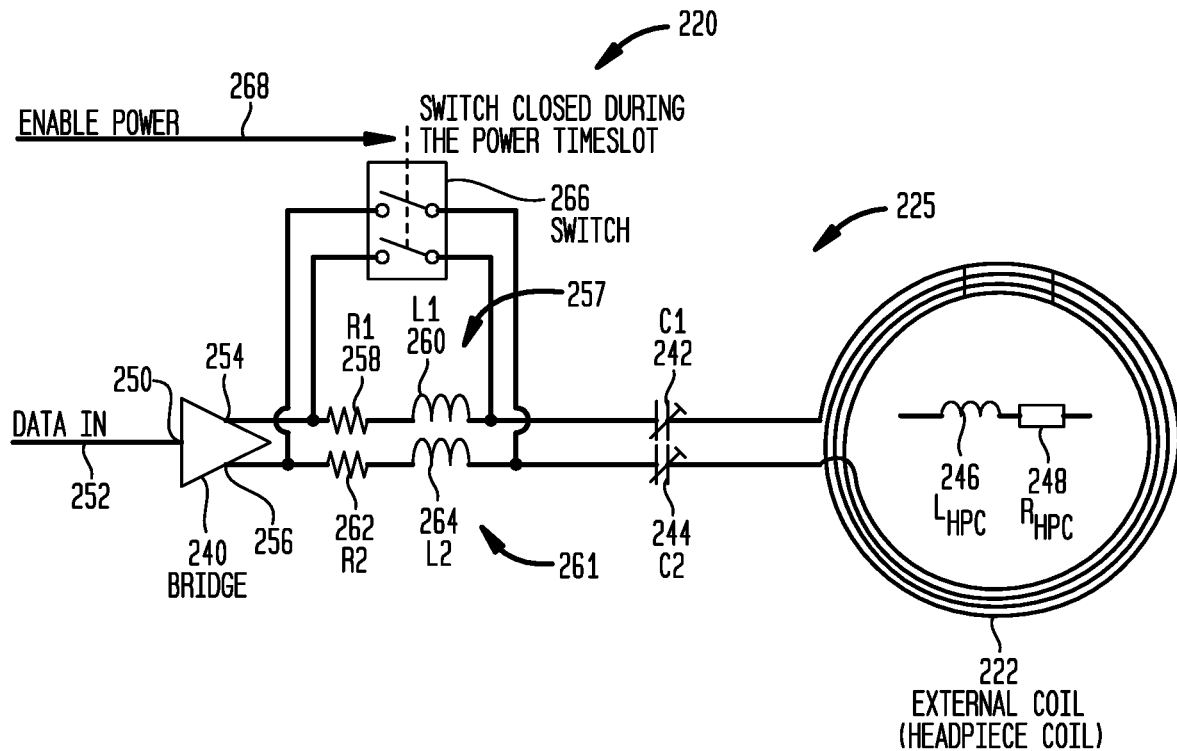
FIG. 2A is a simplified schematic diagram of an external transmitter circuit configured to implement separated power and data transfer techniques in accordance with embodiments presented herein.

FIG. 2A is a schematic diagram illustrating a transmitter circuit 220 configured to separately transfer power and data signals from an external component of an implantable component via a single external coil 222. In the embodiment of FIG. 2A, the external coil 222 is part of an external resonant tank circuit 225 that also comprises capacitor 242 (capacitor C1) and capacitor 244 (capacitor C2). In practice, external coil 222 has an inductive component ($L_{HPC}$) 246 and some small copper losses represented as the series resistive component ($R_{HPC}$) 248.

The transmitter circuit 220 comprises a driver bridge 240. In certain embodiments, the driver bridge 240 is a full H-bridge driver. In other embodiments, the driver bridge 240 is a half H-bridge driver. The driver bridge 240 includes an input 250 that receives an input signal 231 (FIG. 2B) via a data input line 252. The driver bridge 240 also comprises a first output 254 and a second output 256 (differential output). The first output 254 is connected to capacitor 242 (which is connected to external coil 222) via a series circuit 257. The series circuit 257 comprises a resistor 258 (R1) in series with an inductor 260 (L1). The second output 256 is connected to capacitor 244 (which is also connected to external coil 222) via a series circuit 261. The series circuit 261 comprises resistor 262 (R2) in series with an inductor 264 (L2). In an alternative arrangement the driver may only contain a single output (Half H-bridge or single push-pull) connected to a single series circuit comprising a resistor (R1) in series with an inductor 260 (L1).

The first output 254 and the second output 256 of driver bridge 240 are also connected to the capacitors 242 and 244, respectively, via a switch 266. When the switch 266 is closed, the first output 254 is directly connected to capacitor 242 so as to bypass series circuit 257 (i.e., bypass resistor 258 and inductor 260). Similarly, when the switch 266 is closed, the second output 256 is directly connected to capacitor 244 so as to bypass series circuit 261 (i.e., bypass resistor 262 and inductor 264). The switch 266 may be closed in response to an enable power signal 233 (FIG. 2B) received via enable power line 268.

Figure 2B:
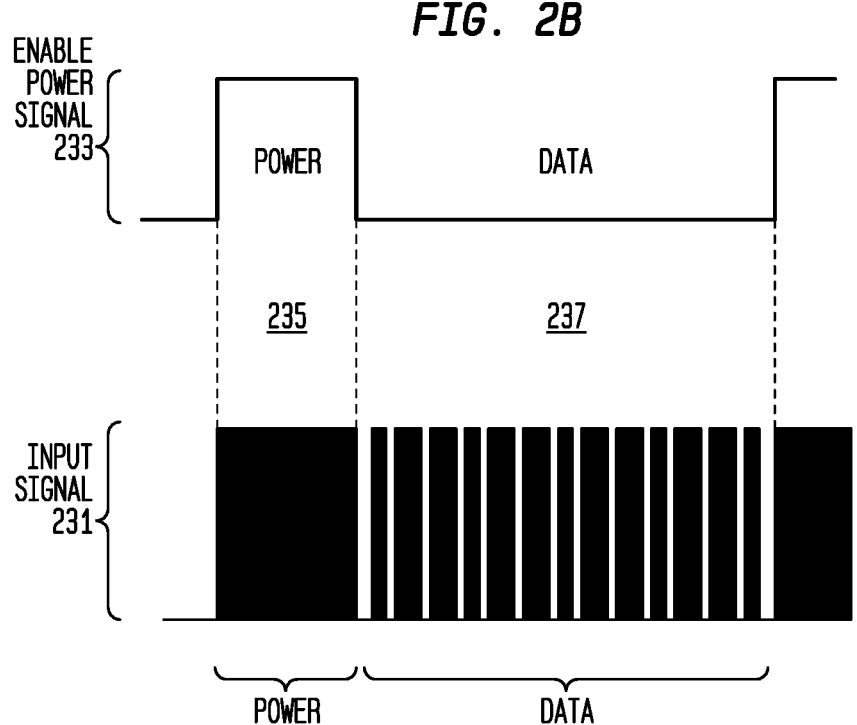
FIG. 2B is a timing diagram illustrating signals supplied to the external transmitter circuit of FIG. 2A.

As noted above, power and data are transmitted during non-overlapping and separate (i.e., different) time slots. FIG. 2B illustrates a power time slot 235 and a data time slot 237 where On-Off keying (OOK) is used to transmit both the power and the data. In OOK, the signal may be either a "1" (i.e., a pulse of energy is present) or a "0" (i.e., no pulse of energy is present). In certain examples, five (5) cycles or pulses may represent a '1' cell and the absence of energy during five (5) cycles may represent a '0' cell. Energy is taken from the '1' cells. As shown in FIG. 2B, during the power time slot 235, the input signal 231 is all 'is,' but switches between '1s' and '0s' during the data time slot 237. The switching between 1s' and '0s' during the data time slot 237 is a digital code that is decoded at the implantable component.

The enable power signal 233 is a pulse waveform that also alternatives between a value of '1' and '0.' During the power time slot 235, the enable power signal 233 has a value of '1' so as to close the switch 266. This causes the outputs 254 and 256 of the driver bridge 240 to be directly connected to the capacitors 242 and 244, respectively, so as to bypass the series circuits 257 (R1 and L1) and 261 (R2 and L2).

Assuming for ease of illustration that the driver bridge 240 and the switch 266 are ideal, the resonance frequency of the external resonant tank circuit 225 during the power time slot ($f_{res\_power\_timeslot}$) is defined below in Equation 1.

$$f_{res\_power\_timeslot} = \frac{1}{2\pi\sqrt{L_{HPC} \cdot \left(\frac{C1 \cdot C2}{C1 + C2}\right)}} \quad \text{Equation 1}$$

In the arrangement where the switch 266 is closed, the quality factor (Q) of the resonant tank circuit 225 during the power time slot ($Q_{ext\_power\_timeslot}$) is defined below in Equation 2.

$$Q_{ext\_power\_timeslot} = \frac{\omega L3}{R_{HPC}} \quad \text{Equation 2}$$

wherein $\omega = 2\pi f \approx 2\pi f_{res}$

Maximum power efficiency is obtained when the quality factor of the external resonant tank circuit 225 during the power time slot is maximized or $R_{HPC}$ is minimized. In order to maximum the quality factor of the external tank circuit during power transfer, the switch 266 is closed during the power time slots 235 so that signals provided by driver bridge 240 bypass the series circuits 257 (R1 and L1) and 261 (R2 and L2), thereby ensuring that the quality factor and of the external resonant tank circuit 225 is not affected (reduced) by the series circuits 257 and 261.

Additionally, the external coil current is maximized when the resonant frequency of the resonant tank circuit 225 during the power time slot is substantially equal or close to the operating frequency ($f_o$) of the external coil 222 (i.e., drive more current through the external coil while maintaining the driver at the same voltage). Therefore, the frequency of the external resonant tank circuit 225 is set (via tuning of capacitors 242 and 244) to be close or equal to the operating frequency to maximize the power efficiency of the transcutaneous link. During the transcutaneous power transfer, the closure of the switch 266 during the power time slots 235 (so that signals provided by driver bridge 240 bypass the series circuits 257 (R1 and L1) and 261 (R2 and L2) ensures that the resonant frequency of the external resonant tank circuit 225 is not affected by the series circuits 257 and 261.

During the data time slots, the switch 266 is opened so that the series circuits 257 (R1 and L1) and 261 (R2 and L2) are placed in series between the driver bridge 240 and the external coil 222. Placing the series circuits 257 and 261 between the driver bridge 240 and the external coil 222 causes a drop in the quality factor of the resonant tank circuit 225, the external coil current, and the resonance frequency. In this case, the resonance frequency of the external resonant tank circuit 225 during the data time slot ($f_{res\_data\_timeslot}$) is defined below in Equation 4.

$$f_{res\_data\_timeslot} = \frac{1}{2\pi\sqrt{(L_{HPC} + L1 + L2)\cdot\left(\frac{C1.C2}{C1+C2}\right)}} \quad \text{Equation 4}$$

Additionally, in the arrangement where the switch 266 is open, the quality factor of the resonant tank circuit 225 during the data time slot ($Q_{ext\_data\_timeslot}$) is defined below in Equation 5.

$$Q_{ext\_data\_timeslot} = \frac{\omega.(L3 + L1 + L2)}{R_{HPC} + R1 + R2} \quad \text{Equation 5}$$

wherein $\omega = 2\pi f \approx 2\pi f_{res}$

It has been discovered that the data integrity improves when the external resonant tank circuit 225 is more dampened (i.e., has a lower quality factor) during data transmission. This is opposed to power transmission where, as noted above, maximum power efficiency is achieved when the quality factor of the resonant tank circuit is maximized. As such, in accordance with the techniques presented herein, the quality factor of the resonant tank circuit is maximized during power transmission, but is purposely lowered during data transmission (i.e., $Q_{est\_data\_timeslot} < Q_{ext\_power\_timeslot}$). The dampened external resonant tank circuit 225 reduces the ringing effects during one or more '0' cycle transitions after a sequence of '1' cycles during use of OOK modulation at $f_0$. The series resistors 258 and 262 operate to dampen the external resonant tank circuit 225 when connected in series between the between the driver bridge 240 and the external coil 222.

It has also been discovered that the data integrity improves and that the external coil current drops during the data time slot when the external resonant tank circuit 225 is tuned lower than the operating frequency. The lower the tuning frequency of the external coil 222 is relative to the operating frequency, the higher the decrease in current flow through the external coil 222 when the driver bridge 222 is acting as a pulsating voltage source (e.g. Class-D driver bridge). As described further below, the decrease in the external coil current prevents interference of the implantable component load with the data recovery at the implantable component. In one example, the operating frequency of the external coil 222 is 5 megahertz (MHz) and the resonant frequency of the external resonant tank circuit 225 during data transmission ($f_{res\_data\_timeslot}$) is set equal to 4.75 MHz). The series inductors 260 and 264 operate to reduce the resonant frequency of the external resonant tank circuit 225 when connected in series between the between the driver bridge 240 and the external coil 222.

Figure 3:
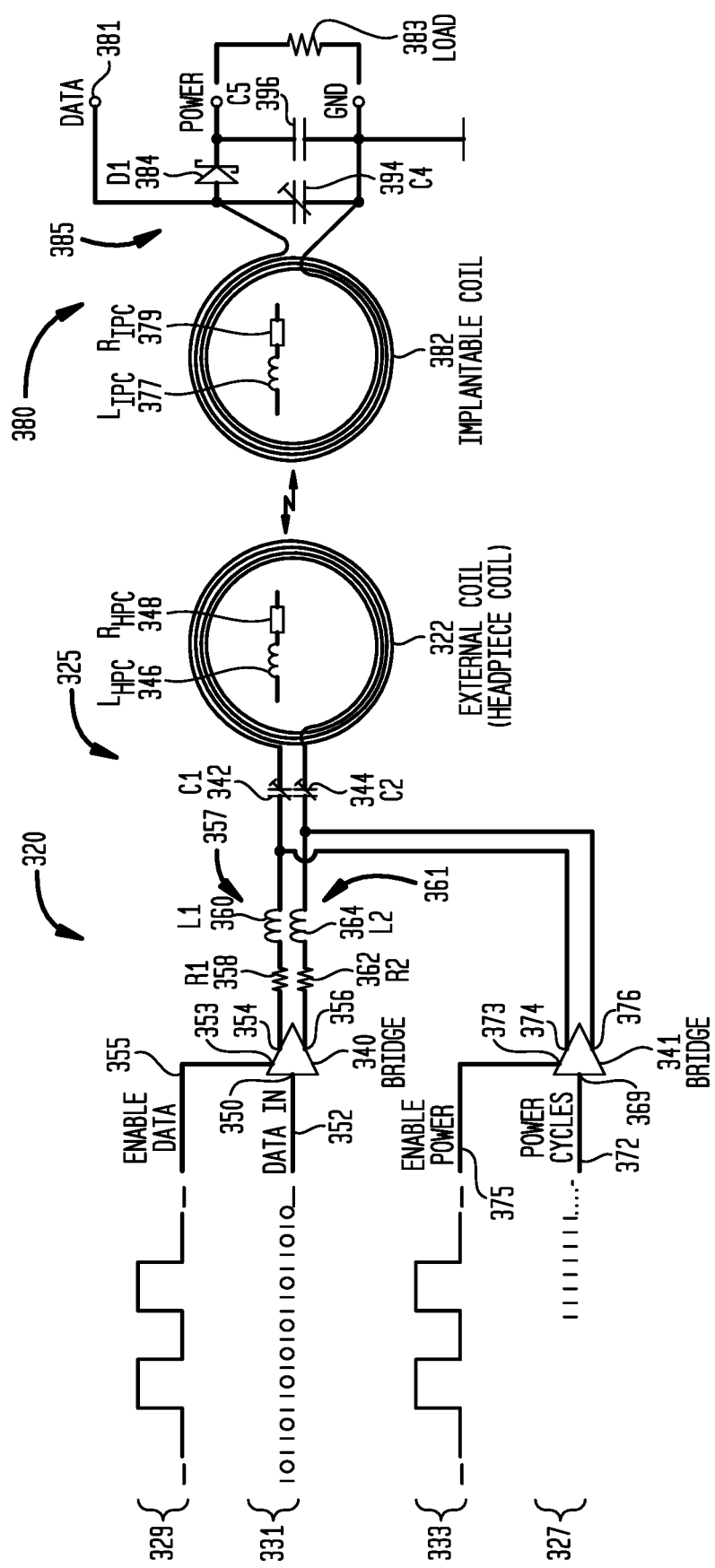
FIG. 3 is a simplified schematic diagram of an external transmitter circuit and an implantable receiver circuit each configured to implement separated power and data transfer techniques in accordance with embodiments presented herein.

As shown in FIG. 2A, the resonance frequency and quality factor during the power time slot and the data time slot are dynamically adjusted through the use of the switch 266. FIG. 3 illustrates an alternative arrangement where a dedicated driver bridge, rather than a switch, is used to dynamically adjust the resonance frequency and quality factor of an external tank circuit.

More specifically, FIG. 3 is a schematic diagram illustrating an external transmitter circuit 320 configured to separately transfer power and data signals to an implantable component via a single external coil 322. In the embodiment of FIG. 3, the external transmitter circuit 320 comprises a first driver bridge 340 (data driver bridge) and a second driver bridge 341 (power driver bridge). As described further below, the driver bridge 340 is enabled during the data time slot, but is deactivated during the power time slot. Similarly, the driver bridge 341 is enabled during the power time slot, but is deactivated during the data time slot. As such, the arrangement of FIG. 3 uses dedicated driver bridges for each of data and power transmission (i.e., the data and power signals have their own driver bridges and only a single driver bridge is enabled at a time).

In the embodiment of FIG. 3, the external coil 322 is part of an external resonant tank circuit 325 that also comprises capacitor 342 (capacitor C1) and capacitor 344 (capacitor C2). In practice, external coil 322 has an inductive component ($L_{HPC}$) 346 and some small copper losses represented as the series resistive component ($R_{HPC}$) 348.

The driver bridge 340 includes an input 350 that receives an input signal 331 via data input line 352 and an enable data input 353 that receives a enable data signal 329 via enable data signal line 355. The driver bridge 340 also comprises a first output 354 and a second output 356. The first output 354 is connected to capacitor 342 (which is connected to external coil 322) via a series circuit 357 that comprises a resistor 358 (R1) in series with an inductor 360 (L1). The second output 356 is connected to capacitor 344 (which is also connected to external coil 322) via a series circuit 361 that comprises resistor 362 (R2) in series with an inductor 364 (L2).

The driver bridge 341 includes an input 369 that receives a power signal 327 via power input line 372 and an enable power input 373 configured to receive an enable power signal 327 via enable power signal line 375. The driver bridge 341 also comprises a first output 374 and a second output 376. The first output 374 is directly connected to capacitor 342 (which is connected to external coil 322) so as to bypass series circuit 357. Similarly, the second output 376 is directly connected to capacitor 344 so as to bypass series circuit 361.

The power signal 327 is a series of all '1' values (consecutive power cycles), while the data input signal 331 switches between '1s' and '0s' (i.e., at 5 MHz a '1' represents five (5) cycles or pulses during 1 μs and a '0' represents a silence during 1 μs for a data rate of 1 Mbps). The enable power signal 333 is a logic signal that alternatives between a value of '1' and '0.' The enable data signal 329 is also a pulse waveform that alternatives between a value of '1' and '0.' The enable signal activates the respective driver at value '1'. However, the enable data signal 329 is the inverse of the enable power signal 333 (note WME: make this more visible in FIG. 3). That is, when the enable power signal 333 is '1', the enable data signal 329 is a '0' value, and vice versa.

In the embodiment of FIG. 3, power and data are transmitted during non-overlapping and separate (i.e., different) time slots using the separate driver bridges. During the data time slots, the enable data signal 329 is high so as to enable driver bridge 340. As such, the outputs 354 and 356, generated using data input signal 331, are used to drive external coil 322. At the same time, the enable power signal 333 is low so as to cause the outputs 374 and 376 of driver bridge 341 to be placed in a high impedance state.

As noted above, the first output 354 is connected to external coil 322 via series circuit 357 (R1 and L1) and the second output 356 is connected to external coil 322 via series circuit 361 (R2 and L2). As such, when driver bridge 340 is enabled, the external coil 322 is driven with signals that pass through series circuit 357 and series circuit 361.

During the power time slots, the enable power signal 333 is high (i.e., a '1' value) so as to enable driver bridge 341. As such, the outputs 374 and 376, generated using power signal 327, are used to drive external coil 322. At the same time, the enable data signal 329 is low (i.e., a '0' value) so as to cause the outputs 354 and 356 of driver bridge 340 to be placed in a high impedance state.

As noted, maximum power efficiency is obtained when the quality factor of the external resonant tank circuit 325 during the power time slot is maximized or $R_{HPC}$ is minimized. Additionally, the external coil current is maximized when the resonant frequency of the resonant tank circuit 325 during the power time slot is substantially equal or close to the operating frequency ($f_0$) of the external coil 322. Therefore, during the power time slots, the bridge 341 is enabled to drive the external coil 322 with signals that pass directly from the outputs 374 and 376 to capacitors 342 and 344, respectively. In this arrangement, the signals bypass the series circuits 357 (R1 and L1) and 361 (R2 and L2), thereby ensuring that the quality factor and resonant frequency of the external resonant tank circuit 325 are not affected by the series circuits 357 and 361.

However, also as noted above, the data integrity improves when the external resonant tank circuit 325 is more dampened (i.e., has a lower quality factor) during data transmission. As such, during the data time slots, the driver bridge 340 is enabled so as to drive external coil 322 with signals that pass through the series circuit 357 (R1 and L1) and series circuit 361 (R2 and L2). That is, the series circuit 357 (R1 and L1) and series circuit 361 (R2 and L2) are placed in between the driver bridge 340 and the external coil 322. Driving the external coil 322 via the series circuits 357 and 361 causes a drop in the quality factor of the resonant tank circuit 325, the external coil current, and the resonance frequency of the resonant tank circuit. It should be noted that R1 and R2 may be an intrinsic part of the data driver bridge.

In summary of FIG. 3, the quality factor of the resonant tank circuit 325 is maximized during power transmission, but is purposely lowered during data transmission (i.e., $Q_{ext\_data\_timeslot} < Q_{ext\_power\_timeslot}$). The dampened external resonant tank circuit 325 reduces the ringing effects during one or more '0' cycle transitions after a sequence of '1' cycles during use of OOK modulation at $f_0$. The series resistors 358 and 362 operate to dampen the external resonant tank circuit 325 when connected in series between the between the driver bridge 340 and the external coil 322.

FIG. 3 also illustrates an implantable receiver circuit 380 configured to receive separate power and data signals transmitted by the external transmitter circuit 320. The implantable receiver circuit 380 comprises an implantable coil 382 that is part of an implantable (internal) resonant tank circuit 385 that also comprises capacitor 394 (capacitor C4) and capacitor 396 (capacitor C5). In practice, implantable coil 382 has an inductive component ($LI_{PC}$) 377 and some small copper losses represented as the series resistive component ($RI_{PC}$) 379. The implantable receiver circuit 380 also comprises a data output 381, a load 383 (i.e., battery or other energy storage device), and an energy rectifier connected between the implantable coil 382 and the load 383. In certain embodiments, the energy rectifier 384 is a diode.

The implantable receiver circuit 380 is described in relation to external transmitter circuit 320. It is to be appreciated that the implantable receiver circuit 380, or variants thereof, may be used with the other external transmitter circuits described herein.

Returning to the embodiment of FIG. 3, it has also been discovered that the data integrity improves and that the current through external coil 322 drops when the external resonant tank circuit 325 is tuned lower than the operating frequency. The lower the tuning frequency of the external coil 322 is relative to the operating frequency, the higher the decrease in current flow through the external coil 322 when the driver bridge 340 is acting as a pulsating voltage source. In one example, the operating frequency of the external coil 322 is 5 MHz and the resonant frequency of the external resonant tank circuit 325 during data transmission ($f_{res\_data\_timeslot}$) is set equal to 4.75 MHz). The series inductors 360 and 364 operate to reduce the resonant frequency of the external resonant tank circuit 325 when connected in series between the between the driver bridge 340 and the external coil 322.

The decrease in the external coil current in response to the detuning of the resonant frequency prevents interference of the implantable component load 383 with the data recovery at the implantable receiver circuit 380. More specifically, the detuning lowers the peak amplitude of the data signals so that the diode 384 is maintained in reverse polarization (i.e., non-conducting during data transmission), thereby preventing the load 383 from being seen at the data output 381.

In certain embodiments, the driver bridge 341 is constructed as a full H-bridge driver, while the driver bridge 340 is a half H-bridge driver. The use of a half H-bridge driver lowers the peak amplitude of the data signal, thereby assisting in maintaining the diode 384 in reverse polarization. Fine adjustments to the received implant voltage level may also be accomplished by altering the pulse width of each RF cycle during the data and power time slot or adapting the driver bridge supply voltages.

Figure 4:
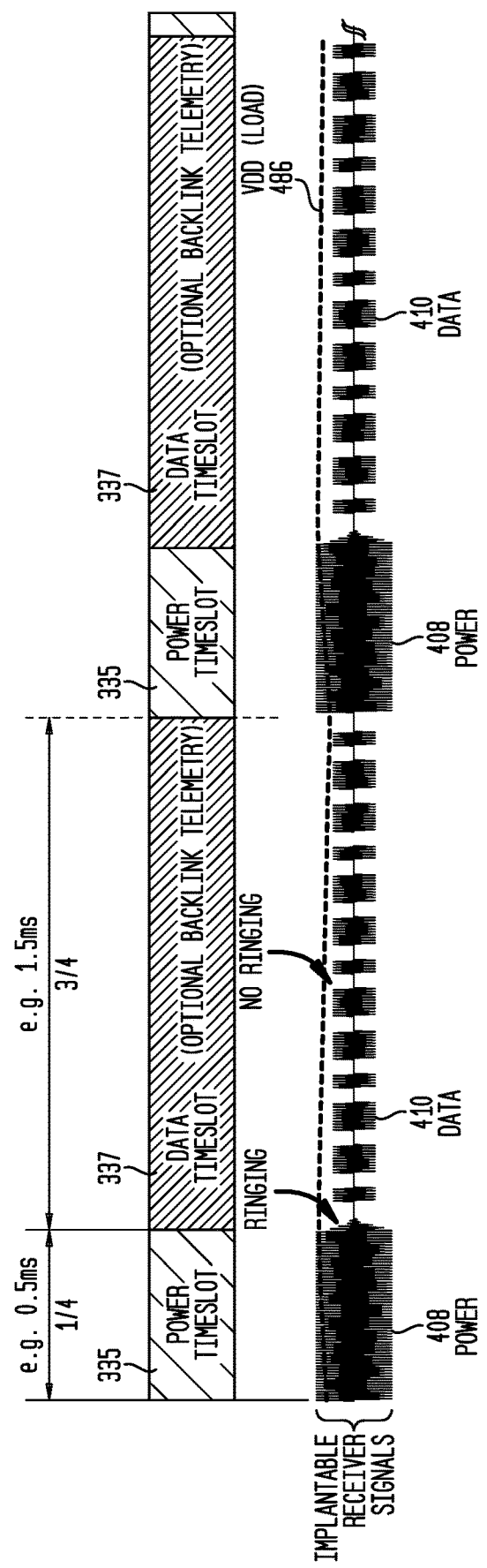
FIG. 4 is a timing diagram illustrating signals observed at the implantable receiver circuit of FIG. 3 during the separated power and data transfer techniques.

FIG. 4 is a diagram illustrating the signal observed at the implantable receiver circuit 380 during power time slots 335 and data time slots 337. In the illustrative example of FIG. 4, the power time slots 335 are approximately 0.5 milliseconds (ms) in length, while the data time slots are approximately 1.5 ms in length (i.e., the power time slots 335 occupy approximately ¼ of the time while the data time slots 337 occupy approximately ¾ of the time).

The implant voltage (VDD) at load 383 is represented in FIG. 4 as dotted line 386. As shown, during the power time slots 335, the implantable receiver circuit 380 receives all '1' signals. As a power time slot 335 ends and a subsequent data time slot 335 begins, ringing is observed at the implantable receiver circuit 380. This ringing is a result of the high quality factor and efficiency of the external resonant tank circuit 325 during transmission of the power signals 388. During the data time slots 335, the ringing is eliminated by reducing the quality factor of the external resonant tank circuit 325.

As described above, the peak amplitude of the data signals 410 is reduced from the peak amplitude of the power signals 408. As shown in FIG. 4, the peak amplitude of the data signals 410 is reduced so as to stay below the implant voltage 486 so that the implant voltage is not observed during the data time slots 337 (i.e., so that the diode 384 remains in reverse polarization).

It is to be appreciated that the data time slots 337 may not be fully filled (i.e., the number of signals sent may depend on the amount of data that needs to be transferred from the external component to the implantable component). In certain embodiments, all or part of a data time slot 337 may be used for backlink telemetry where data is sent from the implantable component to the external component. As such, the external transmitter circuit 320 and the implantable receiver circuit 380 are, in practice, both transceiver circuits.

Figure 5:
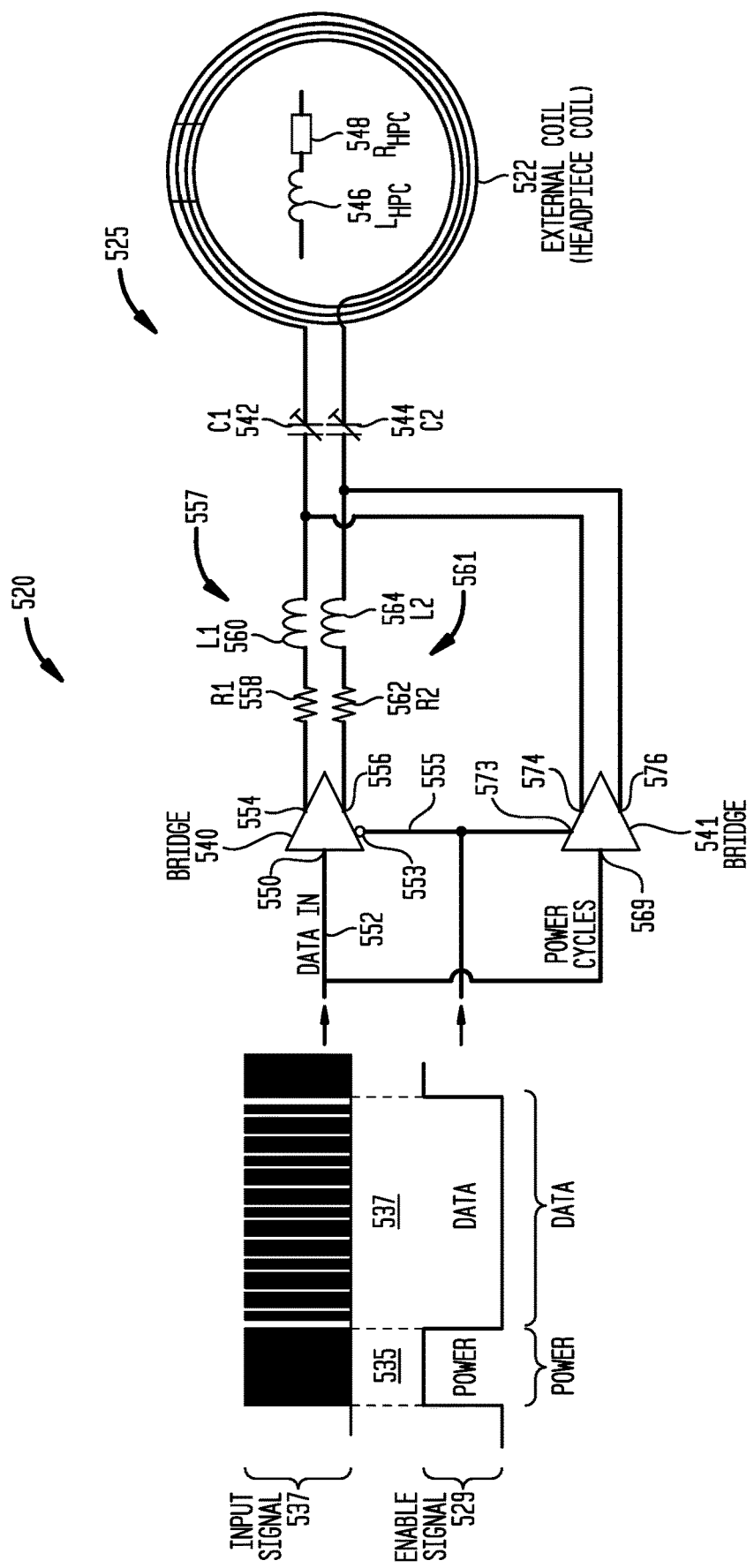
FIG. 5 is a simplified schematic diagram of another external transmitter circuit configured to implement separated power and data transfer techniques in accordance with embodiments presented herein.

FIG. 5 is a schematic diagram illustrating another external transmitter circuit 520 configured to separately transfer power and data signals to an implantable component via a single external coil 522 in accordance with embodiments presented herein. Similar to the embodiment of FIG. 3, the external transmitter circuit 520 uses dedicated driver bridges for each of data and power transmission (i.e., the data and power signals have their own driver bridges and only a single driver bridge is enabled at a time). However, as described further below, the separate driver bridges are driven differently than as shown in FIG. 3.

In the embodiment of FIG. 5, the external transmitter circuit 520 comprises a first driver bridge 540 (data driver bridge) and a second driver bridge 541 (power driver bridge) that are each separately connected to the external coil 522. The external coil 522 is part of an external resonant tank circuit 525 that also comprises capacitor 542 (capacitor C1) and capacitor 544 (capacitor C2). In practice, external coil 522 has an inductive component ($L_{HPC}$) 546 and some small copper losses represented as the series resistive component ($R_{HPC}$) 548.

The driver bridge 540 includes an input 550 that receives an input signal 531 via input signal line 552 and an enable input 553 that receives an enable signal 529 via enable signal line 555. As described further below, the enable input 553 is an inverting input.

The driver bridge 540 also comprises a first output 554 and a second output 556. The first output 554 is connected to capacitor 542 (which is connected to external coil 522) via a series circuit 557 that comprises a resistor 558 (R1) in series with an inductor 560 (L1). The second output 556 is connected to capacitor 544 (which is also connected to external coil 522) via a series circuit 561 that comprises resistor 562 (R2) in series with an inductor 564 (L2).

The driver bridge 541 includes an input 569 that receives the signal 531 via input line 552. The driver bridge 541 also comprises an enable input 573 configured to receive the enable signal 529 via enable signal line 555. In other words, the driver bridge 541 is connected to the same input signal line and the same enable signal as the driver bridge 540. The driver bridge 541 also comprises a first output 574 and a second output 576. The first output 574 is directly connected to capacitor 542 (which is connected to external coil 522) so as to bypass series circuit 557. Similarly, the second output 576 is directly connected to capacitor 544 so as to bypass series circuit 561.

In the embodiment of FIG. 5, power and data are transmitted during non-overlapping and separate (i.e., different) time slots using the separate driver bridges 540 and 541. As shown, the input signal 531 is a series of all '1' values or consecutive RF cycles during a power time slot 535. However, during a data time slot 537, the input signal 531 switches between '1s' and '0s' (i.e., is a digital code representing the OOK modulation). The enable signal 529 is a logic signal that alternatives between a value of '1' and '0.' The enable signal 529 has a vale of '1' during the power time slots 535 and a value of '0' during the data time slots 537.

Additionally, during the power time slots, the enable signal 529 is high (i.e., a '1' value) so as to enable driver bridge 541. As such, the outputs 574 and 576, generated using input signal 531, are used to drive external coil 522. As noted, the input 553 of driver bridge 540 is an inverting input. Therefore, when the enable signal 529 is high, the inverting input 553 will cause the driver bridge 540 to interpret the enable signal 529 as low (i.e., '0' value). This causes the outputs 554 and 556 of driver bridge 540 to be placed in a high impedance state.

During the data time slots, the enable signal 529 is low so as to cause the outputs 574 and 576 of driver bridge 541 to be placed in a high impedance state. However, when the enable signal 529 is low, the inverting input 553 will cause the driver bridge 540 to interpret the enable signal 529 as a high value. As such, the outputs 554 and 556, generated using input signal 531, are used to drive external coil 522.

As noted above, the first output 554 is connected to external coil 522 via series circuit 557 (R1 and L1) and the second output 556 is connected to external coil 522 via series circuit 561 (R2 and L2). As such, when driver bridge 540 is enabled, the external coil 522 is driven with signals that pass through series circuit 557 and series circuit 561.

Maximum power efficiency is obtained when the quality factor of the external resonant tank circuit 525 during the power time slot is maximized or RHPC is minimized. Additionally, the external coil current is maximized when the resonant frequency of the resonant tank circuit 525 during the power time slot is substantially equal or close to the operating frequency ($f_0$) of the external coil 522. Therefore, as noted above, during the power time slots, the bridge 541 is enabled to drive the external coil 522 with signals that pass directly from the outputs 574 and 576 to capacitors 542 and 544, respectively. In this arrangement, the signals bypass the series circuits 557 (R1 and L1) and 561 (R2 and L2), thereby ensuring that the quality factor and resonant frequency of the external resonant tank circuit 525 are not affected by the series circuits 557 and 561.

However, the data integrity improves when the external resonant tank circuit 525 is more dampened (i.e., has a lower quality factor) during data transmission. As such, during the data time slots, the driver bridge 350 is enabled so as to drive external coil 522 with signals that pass through the series circuit 557 (R1 and L1) and series circuit 561 (R2 and L2). That is, the series circuit 557 (R1 and L1) and series circuit 561 (R2 and L2) are placed in between the driver bridge 540 and the external coil 522. Driving the external coil 522 via the series circuits 557 and 561 causes a drop in (i.e., damp) the quality factor of the resonant tank circuit 525, the external coil current, and the resonance frequency.

In summary of FIG. 5, the quality factor of the resonant tank circuit 525 is maximized during power transmission, but is purposely lowered during data transmission (i.e., $Q_{ext\_data\_timeslot} < Q_{ext\_power\_timeslot}$). The dampened external resonant tank circuit 525 reduces the ringing effects during one or more '0' cycle transitions after a sequence of '1' cycles during use of OOK modulation at $f_0$. The series resistors 558 and 562 operate to dampen the external resonant tank circuit 525 when connected in series between the between the driver bridge 540 and the external coil 522.

Additionally, it has also been discovered that the external coil current drops during the data time slot when the external resonant tank circuit 525 is tuned lower than the operating frequency. The lower the tuning frequency of the external coil 522 is relative to the operating frequency, the higher the decrease in current flow through the external coil 522 when the driver bridge 540 is acting as a pulsating voltage source. As described elsewhere herein, the decrease in the external coil current prevents interference of the implantable component load with the data recovery at the implantable component. In one example, the operating frequency of the external coil 522 is 5 MHz and the resonant frequency of the external resonant tank circuit 525 during data transmission ($f_{res\_data\_timeslot}$) is set equal to 4.75 MHz). The series inductors 560 and 564 operate to reduce the resonant frequency of the external resonant tank circuit 525 when connected in series between the between the driver bridge 540 and the external coil 522.

Figure 6:
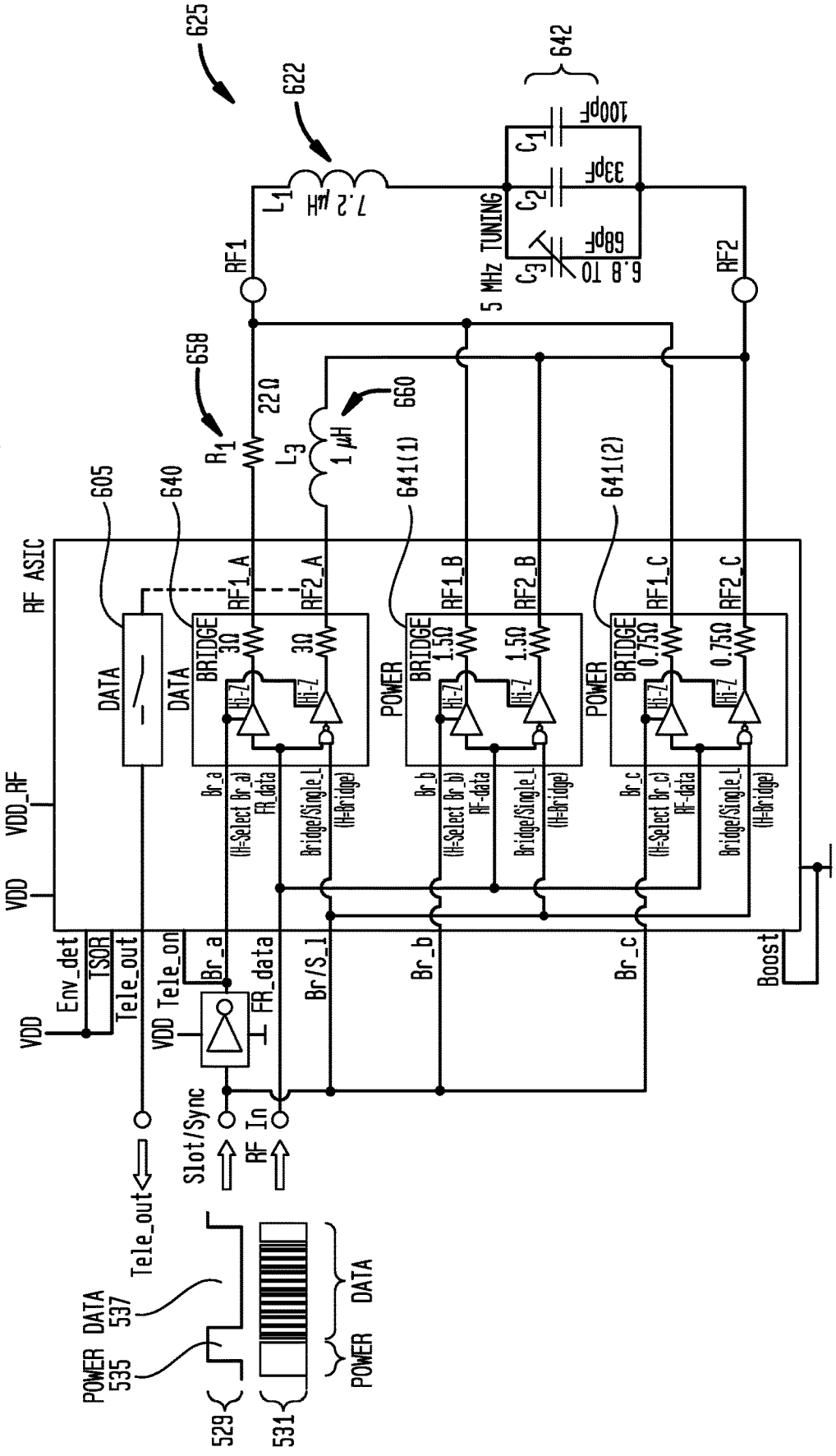
FIG. 6 is a simplified schematic diagram of another external transmitter circuit configured to implement separated power and data transfer techniques in accordance with embodiments presented herein.

FIG. 6 is simplified schematic diagram illustrating another external transmitter circuit 620 configured to separately transfer power and data signals to an implantable component via a single external coil 622 in accordance with embodiments presented herein. Similar to the embodiment of FIG. 5, the external transmitter circuit 620 uses dedicated driver bridges for each of data and power transmission. However, in the embodiment of FIG. 6, two (2) bridges are dedicated for use during power time slots, while a single separate driver bridge is used during the data time slots.

The external transmitter circuit 620 comprises a data driver bridge 640 and two power driver bridges 641(1) and 641(2). The external coil 622 is part of an external resonant tank circuit 625 that comprises capacitors 642 (capacitors C1, C2, and C3). The driver bridges 640, 641(1), and 641(2) receive an input signal 531 (described above with reference to FIG. 5) and an enable signal 529 (also described above with reference to FIG. 5). The enable signal 529 is inverted before reaching data bridge 640. The driver bridge 640 may be a half H-bridge driver, while the driver bridges 641(1) and 641(2) may be full H-bridge drivers.

During the power time slot 535 (FIG. 5), the full H-bridge drivers 641(1) and 641(2) are activated and the outputs of the full H-bridge drivers are used to drive the external coil 622. At the same time, due to the inversion of the enable signal 529, the half H-bridge driver 640 is deactivated and the outputs of the half H-bridge driver are placed in a high impedance state. Placing the full H-bridge drivers 641(1) and 641(2) in parallel to operate simultaneously lowers the conductive losses at the output (relative to a single driver arrangement), thereby further increasing the quality factor of the tank circuit.

During the data time slot 537 (FIG. 5) the half H-bridge driver 640 is activated and the outputs of the half H-bridge driver are used to drive the external coil 622. As shown in FIG. 6, a resistor 658 and an inductor 660 are connected between the outputs of the half H-bridge driver 640 and the external coil 622. The positioning of the resistor 658 and an inductor 660 between the half H-bridge driver 640 and the external coil 622 during data transmission will (1) dampen the resonant tank circuit 625 as described above and (2) lower the signal level of the data pulses received by the implant resulting in a non-conducting energy rectifier as described above.

As noted, backlink telemetry is possible in accordance with embodiments presented herein. FIG. 6 illustrates a switch 605 that is closed when data is received at the external transmitter circuit 620 from an implantable component. In essence, the switch 605 bypasses the unidirectional driver bridges 640, 641(1), and 641(2) during backlink telemetry. Similar switches may be present in the embodiments of FIGS. 2A, 3, 4, and 5, but have been omitted from those FIGS. for ease of illustration.

In summary of FIG. 6, the quality factor of the resonant tank circuit 625 is maximized during power transmission because the outputs of the full H-bridge drivers 641(1) and 641(2) are directly connected to the resonant tank circuit 625. However, the quality factor of the resonant tank circuit 625 is purposely lowered during data transmission. The dampened external resonant tank circuit 625 reduces the ringing effects during one or more '0' cycle transitions after a sequence of '1' cycles during use of OOK modulation at L. The resistor 658 operates to dampen the external resonant tank circuit 625 when connected in series between the between the driver bridge 640 and the external coil 622.

Additionally, the external resonant tank circuit 625 is tuned lower than the operating frequency. As described elsewhere herein, the decrease in the external coil current prevents interference of the implantable component load with the data recovery at the implantable component. In one example, the operating frequency of the external coil 622 is 5 MHz and the resonant frequency of the external resonant tank circuit 625 during data transmission ($f_{res\_data\_timeslot}$) is set equal to 4.75 MHz). The inductor 660 operates to reduce the resonant frequency of the external resonant tank circuit 625 when connected in series between the between the driver bridge 640 and the external coil 622.

Embodiments have been primarily described above with reference to adjustments to the operational characteristics of an external resonant tank circuit. However, it is to be appreciated that adjustments to the operational characteristics of an implantable (internal) resonant tank circuit may be made in addition to, or in place of, the above adjustments to an external resonant tank circuit during the separated power and data transfer techniques.

Figure 7:
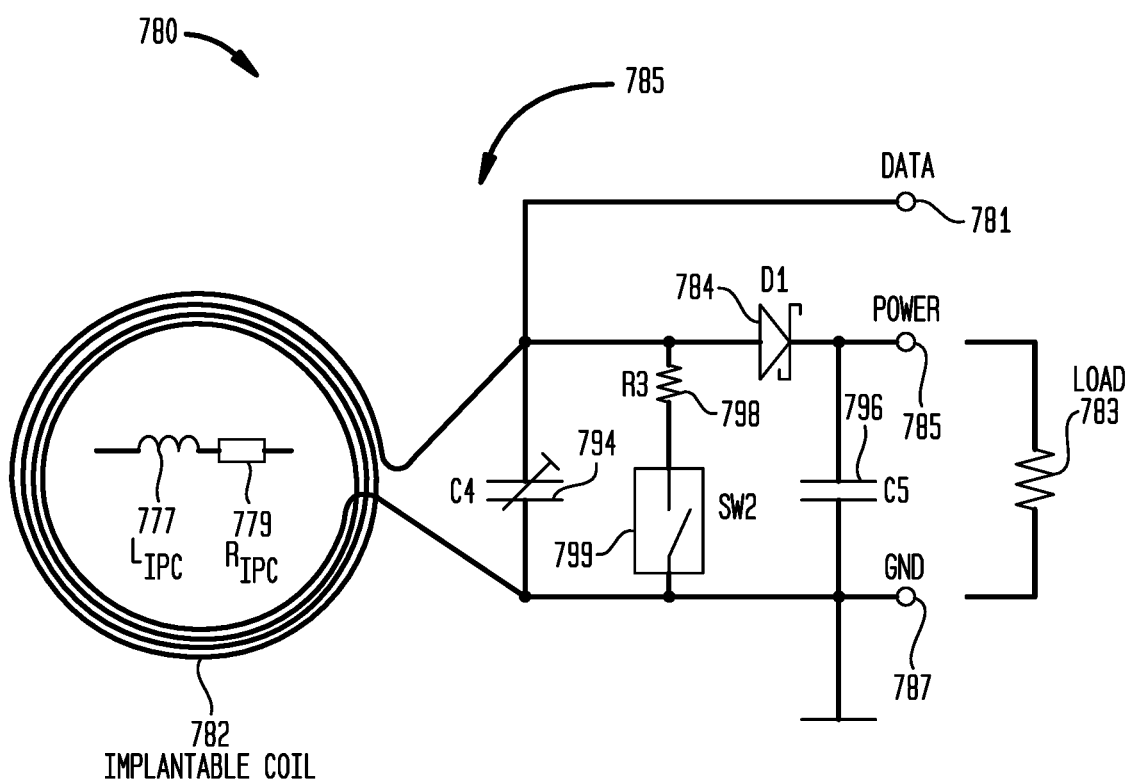
FIG. 7 is a simplified schematic diagram of an implantable receiver circuit configured to implement separated power and data transfer techniques in accordance with embodiments presented herein.

More specifically, FIG. 7 illustrates an implantable receiver circuit 780 configured to receive separate power and data signals transmitted by an external transmitter circuit (not shown). The implantable receiver circuit 780 comprises an implantable coil 782 that is part of an implantable (internal) resonant tank circuit 785 that also comprises capacitor 794 (capacitor C4) and capacitor 796 (capacitor C5). In practice, implantable coil 792 has an inductive component ($LI_{PC}$) 777 and some small copper losses represented as the series resistive component ($RI_{PC}$) 779. The implantable receiver circuit 780 also comprises a data output 781, a load 783 (i.e., battery or other energy storage device) connected between a power terminal 785 and a ground terminal 787, and an energy rectifier 784 connected between the implantable coil 782 and the load 783. In certain embodiments, the energy rectifier 784 is a diode.

The implantable receiver circuit 780 also comprises a resistor 798 and a switch 799 connected in parallel to the capacitor 794. During a data time slot (i.e., when data is received at the implantable coil 782), the switch 799 is closed. When the switch 799 is closed, the resistor 798 is connected to the implantable resonant tank circuit 785. The resistor 798 operates to dampen the implantable resonant tank circuit 785. In other words, the resistor 798 functions to reduce the quality factor of the implantable resonant tank circuit 785 during data reception.

In certain embodiments, a method for transmitting power from an external transmitter circuit to an implantable receiver circuit is provided. The external transmitter circuit comprises an external resonant circuit that includes an external coil, while the implantable receiver circuit comprise an implantable resonant circuit that includes an implantable coil. The method comprises driving the external resonant circuit with one or more driver bridges during a power time slot to cause the external coil to transfer power to the implantable receiver circuit. The method further comprises driving the external resonant circuit with one or more driver bridges during a data time slot to cause the external coil to transfer data to the implantable receiver circuit. The power and data time slots are different time slots and the external resonant circuit is driven such that the quality factor of the external resonant circuit is lower during the data slot than during the power time slot. In certain examples, the the external resonant circuit and the implantable resonant circuit are resonant tank circuits.

In certain examples, the method further comprises driving the external resonant circuit with one or more driver bridges during the data time slot such that a resonance frequency of the external resonant circuit is adjusted during the data time slot so as to be lower or higher than the resonant frequency of the external circuit during the power time slots. In further examples, the method further comprises driving the external resonant circuit with one or more driver bridges during the data time slot such that a peak amplitude of current used to drive the external coil during the data time slots is lower than a peak amplitude of current used to drive the external coil during the power time slots.

In other examples, the implantable receiver circuit comprises an energy rectifier and the method further comprises driving the external resonant circuit with one or more driver bridges during the data time slot such that the peak amplitude of current used to drive the external during the data time slot is such that the energy rectifier does not allow current to pass there through during the data time slots.

As noted above, presented herein are techniques to separately transfer power and data from an external device to an implantable component using a single external coil and a single implantable coil. The external coil is part of an external resonant tank circuit, while the implantable coil is part of an implantable resonant tank circuit. The external coil is configured to transcutaneously transfer power and data to the implantable coil using separate power and data time slots. At least one of the external or internal resonant tank circuit is substantially more damped during the data time slot than during the power time slot.

The techniques presented herein provide high efficiency power transfers (e.g., 40% efficiency over a 12 mm thick skin flap thickness) without affecting the data integrity. High efficiently power transfers may reduce the number of implantable batteries needed, increase autonomy of the implantable component, and enable use of implantable components with larger skin flaps In certain embodiments, the data link can be considered as a Magnetic Induction (MI) radio system over, for example, 5 MHz and could accept data from the bilateral implant during the data time slot. Additionally, ringing effects are substantially eliminated during data transfer due to the damped external tank circuit. The techniques presented herein may also provide stable waveforms shapes during data time slots received by the implant and almost independent of coupling factor, implant load, data time slot duration or frame occupation.

In certain embodiments, the data link can support other modulation types. As amplitude ringing is a phenomena typically observed in OOK modulation other modulation types such as FSK or PSK may also suffer from excessive phase ringing or distortion due to insufficient dampening during the data time slot.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An apparatus, comprising:
an external resonant circuit comprising an external coil; and
one or more driver bridges configured to cause the external coil to transfer power and data to an implantable receiver circuit using separate power and data time slots, wherein the one or more driver bridges comprise at least one data driver bridge that is used to drive the external coil during the data time slots and at least one power driver bridge that is used to drive the external coil during the power time slots;
a first series circuit comprising a first resistor and a first inductor connected between a first output of the at least one data driver bridge and the external resonant circuit
a second series circuit comprising a second resistor and a second inductor connected between a second output of the at least one data driver bridge and the external resonant circuit,
wherein the at least one power driver bridge is connected to the external resonant circuit so as to bypass the first and second series circuits, and
wherein the quality factor of the external resonant circuit is controlled to be lower during the data slots than during the power time slots by de-tuning the external resonant circuit using at least one of capacitance and inductance.

2. The apparatus of claim 1, wherein the external resonant circuit is a resonant tank circuit.

3. The apparatus of claim 1, wherein a resonance frequency of the external resonant circuit is adjusted during the data time slot so as to be lower or higher than the resonant frequency of the external circuit during the power time slots.

4. The apparatus of claim 3, wherein the resonance frequency of the external resonant circuit is adjusted during the data time slots by selectively adding one or more inductive or capacitive components to the external resonant tank circuit.

5. The apparatus of claim 4, wherein the resonance frequency of the external resonant circuit is adjusted during the data time slots by selectively connecting one or more inductors, in series, between the one or more driver bridges and the external coil.

6. The apparatus of claim 3, wherein the resonance frequency of the external resonant circuit is adjusted during the data time slots by selectively removing one or more inductive or capacitive components from the external resonant tank circuit.

7. The apparatus of claim 1, wherein a peak amplitude of current used to drive the external coil during the data time slots is lower than a peak amplitude of current used to drive the external coil during the power time slots.

8. The apparatus of claim 7, wherein the implantable receiver circuit comprises an energy rectifier, and wherein the peak amplitude of current used to drive the external during the data time slot is such that the energy rectifier does not allow current to pass there through during the data time slots.

9. The apparatus of claim 1, wherein the at least one power driver bridge comprises first and second power driver bridges configured to be simultaneously enabled.

10. The apparatus of claim 1, wherein the one or more drivers comprise a first dedicated driver bridge that is used to drive the external coil during the data time slots and a second dedicated driver bridge that is used to drive the external coil during the power time slots.

11. An apparatus, comprising:
an implantable resonant circuit comprising an implantable coil;
an external resonant circuit comprising an external coil forming a transcutaneous power and data link with the implantable coil; and
at least one driver bridge configured to drive the external coil so as to separately transfer power and data to the implantable coil, wherein the at least one driver bridge comprises at least one data driver bridge that is used to drive the external coil during the transfer of data and at least one power driver bridge that is used to drive the external coil during the transfer of power;
a first series circuit comprising a first resistor and a first inductor connected between a first output of the at least one data driver bridge and the external resonant circuit
a second series circuit comprising a second resistor and a second inductor connected between a second output of the at least one data driver bridge and the external resonant circuit,
wherein the at least one power driver bridge is connected to the external resonant circuit so as to bypass the first and second series circuits, and
wherein operational characteristics of the external resonant circuit are dynamically adjusted during transfer of data to the implantable coil by de-tuning the external resonant circuit using at least one of capacitance and inductance.

12. The apparatus of claim 11, wherein the external resonant circuit and the implantable resonant circuits are resonant tank circuits.

13. The apparatus of claim 11, wherein the quality factor of the external resonant circuit is lower during the transfer of data than during the transfer of power.

14. The apparatus of claim 11, wherein a resonance frequency of the external resonant circuit is adjusted during the transfer of data so as to be lower or higher than the resonant frequency of the external circuit during the transfer of power.

15. The apparatus of claim 14, wherein the resonance frequency of the external resonant circuit is adjusted during the transfer of data by selectively adding one or more inductive components or capacitive components to the resonant tank circuit.

16. The apparatus of claim 11, wherein the at least one power driver bridge comprises first and second power driver bridges configured to be simultaneously enabled.

17. The apparatus of claim 11, further comprising:
a capacitor connected to the implantable coil and forming part of the implantable resonant circuit; and
a resistor connectable in parallel to the capacitor via an implantable switch,
wherein during the transfer of data the implantable switch is closed so as to connect the resistor to the implantable resonant circuit to reduce the quality factor of the implantable resonant circuit, and wherein during the transfer of power the implantable switch is opened so as to disconnect the resistor from the implantable resonant circuit.

* * * * *